United States Patent
Rittinger et al.

(10) Patent No.: US 9,556,136 B2
(45) Date of Patent: Jan. 31, 2017

(54) PROCESS FOR THE DISTILLATION OF A MIXTURE COMPRISING A CYCLIC N-VINYLAMIDE

(71) Applicant: BASF SE, Ludwigshafen (DE)

(72) Inventors: Stefan Rittinger, Mannheim (DE); Regina Vogelsang, Ludwigshafen (DE); Pierre Fournier, Limburgerhof (DE); Anirudh Acharya, Mannheim (DE); Sonja Judat, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/662,890

(22) Filed: Mar. 19, 2015

(65) Prior Publication Data

US 2015/0307466 A1  Oct. 29, 2015

(30) Foreign Application Priority Data

Apr. 29, 2014 (EP) .................................... 14166416

(51) Int. Cl.
  C07D 295/023  (2006.01)
  C08F 26/10  (2006.01)
  C08F 226/10  (2006.01)

(52) U.S. Cl.
  CPC ........... C07D 295/023 (2013.01); C08F 26/10 (2013.01); C08F 226/10 (2013.01)

(58) Field of Classification Search
  CPC .............................. C07D 295/023; C08F 26/10
  USPC .......................................................... 548/401
  See application file for complete search history.

(56) References Cited

U.S. PATENT DOCUMENTS

| 5,683,555 A | * | 11/1997 | Heider | .................... | C07B 63/00 |
| | | | | | 159/49 |
| 5,951,828 A | * | 9/1999 | Winter | ..................... | B01D 3/10 |
| | | | | | 203/1 |
| 2002/0002280 A1 | * | 1/2002 | Bottcher | .............. | C07D 201/18 |
| | | | | | 540/485 |

FOREIGN PATENT DOCUMENTS

| CN | 103012235 A | * | 4/2013 | ......... C07D 207/267 |
| WO | WO 2004/103965 A1 | | 12/2004 | |

* cited by examiner

*Primary Examiner* — Ling Choi
*Assistant Examiner* — Chun-Cheng Wang
(74) *Attorney, Agent, or Firm* — Oblon, McClelland, Maier & Neustadt, L.L.P.

(57) ABSTRACT

A process for the distillation of a mixture which consists to at least 90% by weight of a cyclic N-vinylamide and which comprises a stabilizer, wherein
  a polyether is added to the mixture before or during distillation and
  a product is obtained which consists to at least 99.5% by weight of the cyclic N-vinylamide.

21 Claims, No Drawings

PROCESS FOR THE DISTILLATION OF A MIXTURE COMPRISING A CYCLIC N-VINYLAMIDE

The present invention relates to a process for the distillation of a mixture which consists to at least 90% by weight of a cyclic N-vinylamide and which comprises a stabilizer wherein
 a polyether is added to the starting mixture before or during distillation and
 a product is obtained which consists to at least 99.5% by weight of the cyclic N-vinylamide.

Homo- and copolymers of N-vinylpyrrolidone have many technical applications and are produced in large quantities. A usual process for the production of N-vinylpyrrolidone is the Reppe process which is the addition reaction of acetylene; alternatively N-vinylpyrrolidone may be made by dehydration of N-(2-hydroxyethyl)-2-pyrrolidone. The prior art describes such reactions and the work up of the reaction mixture obtained.

WO 2004/103965 discloses a process for the production of N-vinylpyrrolidone by the dehydration process followed by the work up of the obtained reaction mixture. The reaction mixture which comprises a polymerization inhibitor is purified by crystallization and subsequent rectification.

U.S. Pat. No. 5,683,555 discloses a process for the production of N-vinylpyrrolidone followed by work up of the obtained reaction which includes distillation in a thin film evaporator. According to U.S. Pat. No. 5,683,555 a polyether is added to the reaction mixture before the distillation in the thin film evaporator in order to reduce the viscosity of un-distillable components of the reaction mixture.

During transport and storage the purified N-vinylpyrrolidone obtained by such processes and work up should be stabilized against premature polymerization. For such purpose a polymerization inhibitor may be added. In the polymerization process, however, the presence of an inhibitor would have a negative impact on the yield of homo- or copolymers or might not be acceptable in the product for other reasons. Therefore it is desired that any polymerization inhibitor is removed from N-vinylpyrrolidone to be polymerized completely. This is usually done by a distillation process, in which N-vinylpyrrolidone is distilled of the mixture and the inhibitor remains in the sump.

Due to the high temperature during distillation the problem of premature polymerization becomes more severe than during storage and transport. Even in presence of the inhibitor polymerization occurs and the polymer concentration in the sump increases significantly.

It is object of the present invention to provide a simple and effective process for the distillation of N-vinylpyrrolidone, in particular stabilized n-vinylpyrrolidone, wherein the formation of polymers is significantly reduced and whereby the stabilizer is removed almost totally from the distillation product.

It has been found that such a reduced formation of polymers and removal of stabilizer during distillation of N-vinylpyrrolidone is achieved by the process defined above.

To the Mixture

The process of this invention is a process for the distillation of a mixture which consists to at least 90% by weight of a cyclic N-vinylamide.

The cyclic N-vinylamide may be a single compound or a mixture of different cyclic N-vinylamides, in particular it may be a mixture of isomers or derivatives of a specific cyclic N-vinylamide. Such mixtures may be, for example, obtained from the manufacturing process of a defined cyclic N-vinylamide. As example of cyclic N-vinylamides may be mentioned N-vinylcaprolactam, N-vinylpiperidone, N-vinylpyrrolidone, derivatives thereof and mixtures thereof.

In this patent application N-vinylcaprolactam shall mean a mixture comprising 90 to 100% by weight N-vinylcaprolactam and 0 to 10% by weight derivatives of N-vinylcaprolactam. Such derivatives are in particular compounds wherein one or two, preferably one hydrogen atom bounded to a carbon atom of the ring system is replaced by an alkyl group, in particular a methyl group. Preferably the N-vinylcaprolactam shall mean a mixture comprising 95 to 100% by weight N-vinylcaprolactam and 0 to 5% by weight derivatives of N-vinylcaprolactam, most preferably a mixture comprising 97 to 100% by weight N-vinylcaprolactam and 0 to 3% by weight derivatives of N-vinylcaprolactam.

In this patent application N-vinylpiperidone shall mean a mixture comprising 90 to 100% by weight N-vinylpiperidone and 0 to 10% by weight derivatives of N-vinylpiperidone. Such derivatives are in particular compounds wherein one or two, preferably one hydrogen atom bounded to a carbon atom of the ring system is replaced by an alkyl group, in particular a methyl group. Preferably the N-vinylpiperidone shall mean a mixture comprising 95 to 100% by weight N-vinylpiperidone and 0 to 5% by weight derivatives of N-vinylpiperidone, most preferably a mixture comprising 97 to 100% by weight N-vinylpiperidone and 0 to 3% by weight derivatives of N-vinylpiperidone.

In this patent application N-vinylpyrrolidone shall mean a mixture comprising 90 to 100% by weight N-vinylpyrrolidone and 0 to 10% by weight derivatives of N-vinylpyrrolidone. Such derivatives are in particular compounds wherein one or two, preferably one hydrogen atom bounded to a carbon atom of the ring system is replaced by an alkyl group, in particular a methyl group. Such derivatives may in particular be 3-Methyl-N-vinylpyrrolidon, 4-Methyl-N-vinylpyrrolidon or mixtures thereof. Preferably the N-vinylpyrrolidone shall mean a mixture comprising 95 to 100% by weight N-vinylpyrrolidone and 0 to 5% by weight derivatives of N-vinylpyrrolidone, most preferably a mixture comprising 97 to 100% by weight respectively 98 to 100% by weight N-vinylpyrrolidone and 0 to 3% by weight, respectively 0 to 2% by weight derivatives of N-vinylpyrrolidone.

The cyclic N-vinylamide is preferably N-vinylpyrrolidone as defined in the paragraph above.

The cyclic N-vinylamide, particularly N-vinylpyrrolidone, has preferably been obtained by the Reppe process which is the addition reaction of acetylene and 2-pyrrolidone.

Preferably the cyclic N-vinylamide, particularly the N-vinylpyrrolidone, obtained by the Reppe process has already been purified in order to remove by-products from the Reppe process and unreacted starting materials. Hence the mixture to be distilled comprises unreacted starting materials of the Reppe process (as pyrrolidone in case of N-vinylpyrrolidone) or by-products from the Reppe process which are not covered by the above definitions of the cyclic N-vinylamides only in minor amounts, if at all.

More preferably the mixture to be distilled comprises any unreacted starting materials of the Reppe process (as pyrrolidone in case of N-vinylpyrrolidone) or by-products from the Reppe process which are not covered by the above definitions of the cyclic N-vinylamides in a total amount of 0 to 5% by weight, in particular in amounts of 0 to 2% by weight, most preferred in amounts of 0 to 1%, respectively 0 to 0.5% by weight.

In a preferred embodiment the mixture consist to at least 95%, in a particularly preferred embodiment to at least 97%, in a most particularly preferred embodiment to at least 98% by weight of the cyclic N-vinylamide, in particular N-vinylpyrrolidone as defined above.

The mixture comprises a stabilizer, which is preferably a polymerization inhibitor.

Due to the content of such stabilizer premature polymerization of the cyclic N-vinylamide is inhibited during transport and storage of the starting mixture.

The stabilizer usually has a molecular weight below 1000 g/mol, in particular below 500 g/mol.

The stabilizer may be a single stabilizer or a mixture of different stabilizers.

In a preferred embodiment the stabilizer is a phenol or amine type polymerization inhibitor.

Examples of the phenol type inhibitors may include 2,6-di-t-butyl-4-hydroxytoluene, 2,6-di-t-butyl-p-cresol, butylated hydroxyanisole, stearyl-β(3,5-di-t-butyl-4-hydroxyphenyl)-propionate, 2,2'-methylene-bis (4-methyl-6-t-butylphenol), 4,4'-thiobis (3-methyl-6-t-butyl-phenol), 4,4'-butylidene-bis (3-methyl-6-t-butylphenol), 1,1,3-tris (2-methyl-4-hydroxy-5-t-butylphenyl)butane, 1,3,5-trimethyl-2,4,6-tris (3,5-di-t-butyl-4-hydroxybenzy-1)benzene, and tetrakis[methylene-3-(3',5'-di-t-butyl-4'-hydroxyphenyl)propionate] ethane.

Examples of the amine type polymerization inhibitors may include diallyl amines such as ketone-amine condensates, diallyl diamine, N,N-dimethylbenzylamine, N,N-dimethylaniline, p-N, N-dimethylaminopiperazine; ketone-diallylamine condensates, triethylamine, tri-n-butylamine, N-methylmorphine, phenylendiamine or derivatives of phenylendiamine.

Particularly preferred polymerization inhibitors are phenylendiamine in particular p-phenylene-diamine or derivatives of phenylendiamine, in particular N,N'-di-alkyl-p-phenylendiamines or N,N'-diaryl-p-phenylenediamines like N,N'-di-sec-butyl-p-phenylenediamine (known as Kerobit BPD), N,N'-diethyl-p-phenylenediamine or N,N'-diphenyl-p-phenylenediamine.

In a most preferred embodiment the stabilizer is a N,N'-di-alkyl-p-phenylendiamine, particularly N,N'-di-sec-butyl-p-phenylenediamine (known as Kerobit BPD).

The mixture may, for example comprise from 0.0001% by weight (which is 1 ppm) to 10% by weight of the stabilizer.

Preferably the mixture comprises at least 1 ppm, particularly at least 3 ppm most preferred at least 5 ppm of the stabilizer.

Preferably the mixture comprises not more than 3% by weight, particularly not more than 1% by weight of the stabilizer, more preferably not more than 1000 ppm, most preferably not more than 500 ppm of the stabilizer.

In a particularly preferred embodiment the mixture comprises from 3 ppm to 500 ppm, in particular 3 ppm to 200 ppm, respectively 5 to 100 ppm of the stabilizer.

To the Polyether

According to the process of the present invention a polyether is added to the mixture before or during distillation.

The polyether shall be a compound with at least two ether groups.

Preferred is a polyether of formula I

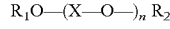

$$R_1O-(X-O-)_n R_2$$

where $R_1$ and $R_2$ independently from one another are hydrogen or a hydrocarbon group with 1 to 10 C atoms, X is a straight-chain or branched $C_2$-$C_6$ alkylene group and n is an integer from 2 to 100.

In a preferred embodiment $R_1$ and $R_2$ independently from one another are hydrogen or an alkyl group with 1 to 10 C atoms.

In a more preferred embodiment $R_1$ and $R_2$ independently from one another are hydrogen or an alkyl group with 1 to 3 C atoms, in particular $R_1$ and $R_2$ are independently from one another are hydrogen or a methyl group.

In a particularly preferred embodiment $R_1$ and $R_2$ are identical.

In a most preferred embodiment $R_1$ and $R_2$ are both hydrogen, which means that the polyether is a polyetherdiol.

X is a straight-chain or branched $C_2$-$C_6$ alkylene group, preferably an ethylene, propylene or butylene group or a mixture thereof.

Particularly preferably X is an ethylene group, a propylene group or a mixture thereof.

More preferably X is an ethylene group.

n is preferably an integer from 2 to 50, in particular from 3 to 50.

Particularly preferably n is an integer from 3 to 20, most preferred from 3 to 15, respectively from 3 to 10.

Polyethers of formula I are commercially available or may easily be synthesized by alkoxylation of diols, for example alkoxylation of ethylenglycol, propylenglycol or butyleneglycol with epoxids as ethylenoxide (EO) or propylenoxide (PO) or mixtures of alkylenoxides in particular mixtures of EO and PO.

As specific examples for polyethylene glycols or polypropylene glycols with a number average molecular weight of 200 to 1000 trade products as Pluriol® 300, Pluriol® 600, or Pluracare® E300 be mentioned.

To the Process

The distillation process of the invention may be performed in any distillation device, for example in a distillation device comprising a distillation column or an evaporator, which is for example a falling film evaporator.

The distillation process of the invention may be performed discontinuously (batch process) or continuously.

In a batch distillation all starting materials are added to the distillation device and the distillation is started thereafter.

In the batch distillation process the polyether is added to the mixture and the obtained combined mixture is distilled, for example in a distillation column.

In a continuously performed distillation process at least some of the starting materials are fed to the running distillation process.

Preferably the process is performed in a distillation device comprising a distillation column or an evaporator and the mixture is continuously fed to the distillation device. The distillation device may comprise further elements, for example hold up vessels. The mixture may be fed directly to the distillation column or the evaporator; it may, for example, also be fed to a hold up vessel and from there to the distillation column or the evaporator.

In a continuously performed distillation process the polyether may be fed continuously to the distillation device as well.

The feed of the mixture and the polyether feed may be fed separately or may be combined to one feed. Preferably 0.01 to 20 parts by weight, in more preferred embodiment 0.05 to 5 parts by weight of the polyether per 100 parts by weight of the mixture are continuously fed to the distillation device.

In a preferred embodiment the distillation device comprises a distillation column.

In a continuously performed distillation process the polyether may also be added in total or partially in advance to the sump of the distillation column, as the polyether is not distilled and remains or concentrates in the sump of the distillation column or evaporator.

The sump may be withdrawn partially from the continuously performed distillation process in amounts to maintain a steady state and may be fed to further work up or combustion.

In both the discontinuously and the continuously performed distillation process the polyether will remain and/or concentrate in the sump of the distillation column or of the evaporator. Preferably the polyether concentration in the sump of the continuously operated distillation column or evaporator is kept at 1 to 90% by weight, particularly preferably at 5 to 80% by weight, in particular 10 to 70% by weight and in most preferred embodiments at 20 to 60, respectively 30 to 60% by weight based on the total weight of the sump. In a batch wise distillation the fore standing concentrations preferably are the concentrations of the polyether at the beginning of the batch distillation.

In a preferred embodiment the distillation process is performed in a distillation device comprising a distillation column.

Preferably the distillation column is operated at a temperature of 50 to 200° C.

The temperature of the sump preferably is from 70 to 180° C., particularly from 100 to 150° C. and more preferably from 115 to 135° C. The temperature of the product (NVP) which is withdrawn from the distillation column is preferably from 70 to 180° C., particularly preferably from 100 to 125° C.

Preferably the distillation is performed at a pressure below 1 bar (reduced pressure). Preferably the pressure is from 1 to 500 mbar, in particular at a pressure of 5 to 200 mbar, more preferably at a pressure of 10 to 200 mbar, respectively 10 to 100 mbar.

Suitable distillation columns are columns with random packing or columns with structured packing.

Also suitable are columns which comprise both random packings and structured packings, for example comprise random packings in defined sections and have structured packing elements (e.g. installed steel sheets) in others.

The distillation column preferably comprise in total at least 2 theoretical stages. The number of theoretical stages may, for example, be 2 to 100 and in particular 2 to 50. With the claimed process 2 to 5 stages, in particular only 2 to 4 and most preferred only 3 stages are sufficient to get best results regarding the purity of the cyclic N-vinylamide, in particular NVP.

In a preferred embodiment the columns are sealed to prevent the ingress of humidity and air.

Preferably the product is distilled off at the top of the column. It may, however, also be withdrawn at any other height of the distillation column, for example in the middle or in the upper part.

Usually the product is subsequently cooled in a condenser. The product may be cooled by an open or closed condensation. Preference is given to a closed condensation; in the case of closed condensation, the product is conducted through the condenser in closed tubes, which are cooled externally.

The sump of distillation column or evaporator comprises any polymers of the cyclic N-vinyl amide formed during distillation. With the process of the invention formation of polymers is significantly reduced due to the presence of the polyether.

To the Product

The product obtained consists to at least 99.5% by weight of the cyclic N-vinylamide.

Preferably the product consists to at least 99.7% by weight, particularly preferably to at least 99.9% by weight and more preferably to at least 99.99% by weight of the cyclic N-vinylamide, which is particularly N-vinylpyrrolidone as defined above.

In case of a stabilizer comprising mixture the product, which is in particular N-vinylpyrrolidone, does comprise no or very low amounts of stabilizer, only. The amount of stabilizer in the product is preferably at maximum 100 ppm, in particular at maximum 10 ppm, usually it is lower than 5 ppm or lower than 1 ppm.

The product may comprise low amounts of acetic acid, which might be due to some content of acetic acid in specific grades of the polyether. Depending of the polyether used, the content of acetic acid in the product may be for example from 0.00001 to 0.1% by weight in particular from 0.00001 to 0.01% by weight of the product. It has been found that a content of acetic acid has no impact on the later use of the product. In particular such amount of acetic acid has no impact on any polymerization or copolymerization of the cyclic N-vinylamide.

The product which is the purified cyclic N-vinyl amide is usually used in radical polymerization processes.

Homo- or copolymers of a cyclic N-vinylamide, in particular of N-vinyl pyrrolidone are obtained by such radical polymerization processes.

By virtue of the process according to the invention, it is possible to obtain cyclic N-vinyl amides with a very high degree of purity. Any stabilizer is removed in total or nearly in total from the cyclic N-vinylamide by the above process.

The process of the invention is very efficient. In particular formation of by-products during distillation, in particular formation of polymers of the cyclic N-vinyl amide, is reduced significantly.

EXAMPLES

Compounds
NVP: N-vinyl pyrrolidone
Kerobit BPD: N,N'-di-sec-butyl-p-phenylenediamine
Pluriol E 300: polyethylenglycol with a molecular weight of 300 g ($R_1$ and $R_2$ in formula I are hydrogen and X is ethylene)

Example 1

A distillation of N-vinylpyrrolidone (NVP) comprising 10 ppm by weight of Kerobit BPD has been performed.

The distillation set-up was a still with a column as rectification section equipped with Rombopak 9M structured packaging from which distillate was withdrawn at the top. The height of the Rombopak 9M packaging was 0.5 meter which corresponds to 3 theoretical stages.

Pluriol E 300 was filled into the still before start of experiments together with a certain amount of the above NVP/Kerobit BPD mixture and additional Kerobit BPD so that the still contained a sump comprising 50 by weight % of Pluriol E 300, 49% NVP and 1% of Kerobit BPD.

10 g/minute of the NVP/Kerobit BPD mixture were continuously fed to the still of the distillation column.

The column was operated at a sump temperature of 126° C. and at a temperature of 104° C. at top of the column and a pressure of 25 at the head and 26 mbar the bottom of the column. At the top of the column NVP was withdrawn (amount: 10 g/minute).

The NVP withdrawn had a purity of at least 99.7% by weight; the content of Kerobit BPD was below 1 ppm.

The Kerobit BPD introduced by the feed was accumulated in the still.

Over a period of 9 days, distillation experiments with the above set-up were performed without exchanging the still content. Each day the sump was heated to operating temperature in the morning. Heating was stopped in the afternoon and the set-up together with the still content cooled down to room temperature.

At each day the distillation process was performed for 6 hours at a sump temperature of 120° C. to 130° C.

After 6 days of distillation (54 operating hours at 120 to 130° C.) no polymer was formed in the sump.

Example 2

1.5 kilogram (kg) Pluriol E 300 were added to the sump of a falling film evaporator.

N-vinylpyrrolidone (NVP) stabilized with Kerobit BPD was tempered at 40° C. for 4 weeks. The resulting mixture comprised of 99.8% by weight of N-vinylpyrrolidone (NVP), 11 ppm Kerobit BPD and approximately 0.05% by weight of PVP.

This mixture was continuously fed to a holdup vessel and then pumped to the falling film evaporator; after about fourteen days (281 operating hours) 400 kg of the mixture had been fed in total, this corresponds to an amount of 200 g PVP.

The falling film evaporator was operated in a temperature range of 100-133° C. and a pressure range of 10-40 mbar (at the bottom of the evaporator).

After fourteen days (281 operating hours) the sump finally had a weight of 1.94 kg and the composition was (in weight %): 7.3% PVP, 39.2% NVP and 53% Pluriol E 300.

Analysis of the distillate samples revealed a concentration of Kerobit BPD in the range of 14 to 21 ppm in the overhead product.

So the total weight of the sump has increased during said running time by 0.44 kg (1.94-1.5 kg) of which about 150 g is PVP. The PVP of the fed mixture has accumulated in the sump; no additional PVP has been formed.

No deposits, no precipitating solids and no fouling could be observed in the falling film evaporator.

The invention claimed is:

1. A process for the distillation of a mixture comprising a stabilizer and at least 90% by weight of a cyclic N-vinylamide based on the total weight of said mixture, the process comprising:
adding a polyether to the mixture before or during distillation to obtain a product comprising at least 99.5% by weight of the cyclic N-vinylamide and at most 10 ppm stabilizer based on the total weight of said product.

2. The process according to claim 1, wherein the cyclic N-vinylamide is N-vinylpyrrolidone (NVP).

3. The process according to claim 1, wherein the mixture comprises at least 98% by weight of the cyclic N-vinylamide based on the total weight of said mixture.

4. The process according to claim 1, wherein the stabilizer is a phenol or amine type polymerization inhibitor.

5. The process according to claim 1, wherein the stabilizer is a N, N'-di-alkyl-p-phenylendiamine.

6. The process according to claim 1, wherein the mixture comprises from 3 to 500 ppm of the stabilizer based on the total weight of said mixture.

7. The process according to claim 1, wherein the polyether is a polyether of formula I

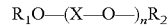

wherein $R_1$ and $R_2$ are each independently hydrogen or a hydrocarbon group with 1 to 10 C atoms, X is a straight-chain or branched $C_2$-$C_6$ alkylene group and n is an integer of from 2 to 100.

8. The process according to claim 7, wherein X is an ethylene or propylene group or a mixture thereof.

9. The process according to claim 7, wherein $R_1$ and $R_2$ in formula I are each independently hydrogen or an alkyl group with 1 to 3 C atoms.

10. The process according to claim 7, wherein $R_1$ and $R_2$ in formula I are each hydrogen.

11. The process according to claim 7, wherein n is an integer of from 2 to 50.

12. The process according to claim 1, wherein the process is performed in a distillation device comprising a distillation column or an evaporator and the mixture is continuously fed to the distillation device.

13. The process according to claim 12, wherein the polyether is also fed continuously to the distillation device.

14. The process according to claim 1, wherein 0.01 to 20 parts by weight of the polyether per 100 parts by weight of the mixture are continuously fed.

15. The process according to claim 12, wherein a sump of the continuously operated distillation column or evaporator comprises 1 to 90% by weight of the polyether based on the total weight of the sump.

16. The process according to claim 15, wherein a temperature of the sump is from 70 to 180° C. and a temperature of the product which is withdrawn from the distillation column is from 70 to 180° C.

17. The process according to claim 1, wherein the distillation is performed at a pressure below 1 bar.

18. The process according to claim 1, wherein the product comprises at least 99.9% by weight of the cyclic N-vinylamide based on the total weight of said product.

19. The process according to claim 1, wherein the product comprises less than 5 ppm of the stabilizer based on the total weight of said product.

20. The process according to claim 1, wherein the product comprises from 0.00001 to 0.1% by weight of acetic acid based on the total weight of said product.

21. A process for making a homo- or copolymer of a cyclic N-vinylamide, wherein said process comprises:
producing a cyclic N-vinylamide by the process according to claim 1, and
radical polymerizing said cyclic N-vinylamide.

* * * * *